United States Patent
Mul et al.

(10) Patent No.: US 11,382,576 B2
(45) Date of Patent: Jul. 12, 2022

(54) ERGONOMIC SUPPORT DEVICE FOR USERS IN MEDICAL ENVIRONMENT

(71) Applicant: KONINKLIJKE PHILIPS N.V., Eindhoven (NL)

(72) Inventors: Jette Mul, Utrecht (NL); Robert Jacobus Maria Kamps, Haarsteeg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/049,552

(22) PCT Filed: Apr. 17, 2019

(86) PCT No.: PCT/EP2019/059870
§ 371 (c)(1),
(2) Date: Oct. 21, 2020

(87) PCT Pub. No.: WO2019/206751
PCT Pub. Date: Oct. 31, 2019

(65) Prior Publication Data
US 2021/0128086 A1   May 6, 2021

(30) Foreign Application Priority Data

Apr. 24, 2018 (EP) .................................... 18168925

(51) Int. Cl.
*A61B 6/10* (2006.01)
*A61B 90/60* (2016.01)
(Continued)

(52) U.S. Cl.
CPC ................ *A61B 6/107* (2013.01); *A47C 3/18* (2013.01); *A47C 7/541* (2018.08); *A47C 7/62* (2013.01);
(Continued)

(58) Field of Classification Search
CPC ................................ A61B 6/107; A61B 90/60
See application file for complete search history.

(56) References Cited

U.S. PATENT DOCUMENTS

| 3,754,787 A | * | 8/1973 | Garber | A61B 90/60 |
| | | | | 297/195.11 |
| 4,460,833 A | * | 7/1984 | Malamud | A61B 6/107 |
| | | | | 250/515.1 |

(Continued)

FOREIGN PATENT DOCUMENTS

| CN | 110037731 A | * | 7/2019 |
| CN | 111227861 A | * | 6/2020 |

(Continued)

OTHER PUBLICATIONS

Albayrak et al:"A Newly Designed Ergonomic Body Support for Surgeons": Surg Endosc (2007), 21: 1835-1840.
(Continued)

*Primary Examiner* — Timothy J Brindley (57) ABSTRACT

The present invention relates to ergonomic supports in medical environment. In order to provide improved ergonomic support while providing a minimum impact of the user's activities, an ergonomic support device (10) for users in medical environment is provided. The support device comprises a seating support arrangement (14), an X-ray shielding arrangement (18) and a base support structure (12). The base support structure provides mechanical support for the seating support arrangement and the X-ray shielding arrangement. The seating support arrangement comprises a seat support surface (16) that is configured for supporting a buttocks area of a user. The X-ray shielding arrangement comprises at least one X-ray shield (20) that is configured for shielding at least a part of an X-ray radiation to which a user is exposed to while supported by the support surface. The at least one X-ray shield is movably mounted to the base (Continued)

support structure to be adjustable in its position relative to a user at least partly resting on the seat support surface.

13 Claims, 6 Drawing Sheets

(51) Int. Cl.
*A47C 7/54* (2006.01)
*A47C 3/18* (2006.01)
*A47C 7/62* (2006.01)
*A47C 9/00* (2006.01)
*A47C 7/00* (2006.01)

(52) U.S. Cl.
CPC .............. *A47C 9/002* (2013.01); *A61B 90/60* (2016.02); *A47C 7/006* (2013.01)

(56) References Cited

U.S. PATENT DOCUMENTS

| | | | | |
|---|---|---|---|---|
| 5,006,718 | A * | 4/1991 | Lenhart | A61B 6/107 250/515.1 |
| 7,829,873 | B2 * | 11/2010 | Fox | A61B 6/107 250/515.1 |
| 9,877,688 | B1 * | 1/2018 | Colling | A61B 6/107 |
| 10,004,466 | B1 * | 6/2018 | Colling | A61B 6/107 |
| 10,643,757 | B1 * | 5/2020 | Colling | A61G 13/10 |
| 2002/0158492 | A1 | 10/2002 | Ko | |
| 2009/0278391 | A1 | 11/2009 | Ulrich | |
| 2018/0220977 | A1 * | 8/2018 | Colling | A47B 96/07 |

FOREIGN PATENT DOCUMENTS

| | | | | |
|---|---|---|---|---|
| CN | 111789683 | A * | 10/2020 | |
| CN | 112472118 | A * | 3/2021 | |
| CN | 112515697 | A * | 3/2021 | |
| CN | 112568926 | A * | 3/2021 | |
| DE | 19643623 | A1 | 4/1998 | |
| DE | 102013203812 | A1 * | 9/2014 | ........... A61B 6/4405 |
| DE | 102016223490 | A1 * | 1/2018 | ............. A61B 6/032 |
| EP | 1477992 | A1 * | 11/2004 | ............. A61B 6/107 |
| JP | S5453879 | A | 4/1979 | |
| JP | 2013128511 | A | 7/2013 | |
| KR | 20210016117 | A * | 2/2021 | |
| KR | 20210027584 | A * | 3/2021 | |

OTHER PUBLICATIONS

Albayrak et al: "Impact of a Chest Support on Lower Back Muscles Activity During Forward Bending"; Applied Bionics and Biomechanics, vol. 7, No. 2, pp. 131-142, 2010.
Fadl et al: "A Review of Spinal Injuries in the Invasive Cardiologist: Part 1. Biomechanics and Pain Generation": Pacing and Clinical Electrophysiology, vol. 30, Issue 8, 2007.
Goldstein et al: "Occupational Hazards of Interventional Cardiologists: Prevalence of Orthopedic Health Problems in Contemporary Practice"; Official Journal of the Society for Cardiac Angiography & Intervention, 2004, 63(4), pp. 407-411.
PCT/EP2019/059870 WO & ISR, Jul. 17, 2019, 14 Page Document.

* cited by examiner

ERGONOMIC SUPPORT DEVICE FOR USERS IN MEDICAL ENVIRONMENT

CROSS-REFERENCE TO PRIOR APPLICATIONS

This application is the U.S. National Phase application under 35 U.S.C. § 371 of International Application No. PCT/EP2019/059870, filed on Apr. 17, 2019, which claims the benefit of European Patent Application No. 18168925.8, filed on Apr. 24, 2018. These applications are hereby incorporated by reference herein.

FIELD OF THE INVENTION

The present invention relates to ergonomic supports, and relates in particular to an ergonomic support device for users in medical environment, to a medical laboratory equipment arrangement and to a method for X-ray imaging of a patient.

BACKGROUND OF THE INVENTION

In medical environments, such as in cathlabs or other operating rooms in a hospital, numerous activities may require a standing or leaning position of a user, i.e. a surgeon, physician or other support personnel, during examinations or interventions of a patient. This may result in substantial physical workload for the user. Further, when X-ray radiation is used such as for imaging a patient, individually worn X-ray protections have to be used which add further weight, thus further increasing the physical workload.

DE 19643623 A1 describes a radiation shield and a saddle seat for supporting behind the shield. The radiation shield is provided with openings through which a seated user may extend his arms. The height of the radiation shield may be adjustable.

JP 2013-128511 A discloses an X-ray protective device to be used by an operator of a medical angiography device or X-ray CT device. A frame is shaped to surround a standing person and is partly open at the rear or on the side. A chair may be provided within the frame. Further, the frame may be provided with an X-ray shield comprising one or more X-ray protective sheets formed so as to surround a person. The sheets are optionally removable for maintenance or replacement.

However, it has been shown that these solutions may restrict the user's activities for example when performing medical interventions in a cathlab.

SUMMARY OF THE INVENTION

There may thus be a need to provide improved ergonomic support having a reduced impact on the user's activities.

This need may be addressed by the subject-matter of the independent claims; further embodiments are incorporated in the dependent claims. It should be noted that the following described aspects of the invention apply also for the ergonomic support device for users in medical environment, for the medical laboratory equipment arrangement and for the method for X-ray imaging of a patient.

According to the present invention, an ergonomic support device for users in medical environment is provided. The support device comprises a seating support arrangement, an X-ray shielding arrangement and a base support structure. The base support structure provides mechanical support for the seating support arrangement and the X-ray shielding arrangement. The seating support arrangement comprises a seat support surface that is configured for supporting a buttocks area of a user. The X-ray shielding arrangement comprises at least one X-ray shield that is configured for shielding at least a part of an X-ray radiation which a user is exposed to while supported by the support surface. The at least one X-ray shield is movably mounted to the base support structure to be adjustable in its position relative to a user at least partly resting on the seat support surface, the at least one X-ray shield being movable from a first position to a second position and vice versa.

This provides flexibility for the user, since the X-ray shield can be moved between different positions. Thus, the device can move from a first position, in which a user can for example easily access the support surface in order to seat himself thereon, to a second position providing effective shielding from X-ray radiation. In other words, the second position provides a user with more shielding from incident radiation, in particular scattered X-ray radiation.

As a result, the seating surface may be easily accessible when a user positions himself for example near an X-ray imaging system, while a relatively high radiation shielding can be provided at other times, for example when the user is seated and such system is in use. Further, for example, the shield may be moved to the first position briefly during an ongoing medical procedure, when a physician needs to have unimpeded access to a patient on the table temporarily.

The term "ergonomic support device" refers to a device that physiologically supports the user. The ergonomic support thus provides physical support for the user. The support provides a load bearing function that provides relief to the user. The load bearing function reduces the resulting loads to be carried by the musculoskeletal system of the user, i.e. the system of primarily bones, muscle and sinews.

For example, the "user" in the medical environment is a physician, e.g. a cathlab physician. The term "cathlab" refers to a catheter laboratory. The cathlab may be provided as an operational room for examination and interventional procedures of patients, such as in a hospital.

The medical environment relates, in particular, to the field of X-ray imaging of other procedures where X-ray radiation is applied. In other examples, other types of radiation are provided for which a shielding is required.

The X-ray shield provides X-ray protection and comprises X-ray absorbing material such as lead or other suitable materials.

The ergonomic support device can also be referred to as an ergonomic support apparatus. The seating support arrangement can also be referred to as a seating support device. The X-ray shielding arrangement can also be referred to as an X-ray shielding device.

The movability of the X-ray shield provides the advantage that a user can take place on the seat support surface even when he/she is wearing a front apron, which may be heavy and which may thus obstruct the user's movement. After being placed, the X-ray shield can be moved in front of the user, i.e. between the user and a potential source of X-ray radiation. During phases of non-use, the X-ray shielding can easily be moved away, e.g. to the side or behind the user to increase freedom of movement for the user.

The ergonomic support is provided for cathlab physicians, but can also be used for other users, e.g. doctors, who have issues with posture. The ergonomic support is also provided for users who have issues with X-ray protection in their working environments, for example, physicians in different medical fields, surgeons, dentists, and also hairdressers, make-up artists, nurses, radiologic technicians and other caretakers who need to achieve a bending posture in relation to a patient while being protected by radiation shielding.

In an example, the ergonomic support device is provided as a retrofit kit for converting a base support structure with a seating support arrangement into an ergonomic support device for users in medical environment. The retrofit kit comprises an X-ray shielding arrangement. The X-ray shielding arrangement is provided with a mounting adapter configured to be mounted to a base support structure providing mechanical support for a seating support arrangement and the X-ray shielding arrangement. The X-ray shielding arrangement comprises at least one X-ray shield that is configured for shielding at least a part of an X-ray radiation which a user is exposed to while supported on a support surface. The at least one X-ray shield is movably mountable to a base support structure to be adjustable in its position relative to a user at least partly resting on the seat support surface.

The seating support arrangement comprises a seat support surface that is configured for supporting a buttocks area (or bottom area) of a user.

In an example of the retrofit kit, the X-ray shield is provided according to one of the examples described above and below.

The at least one X-ray shield is movable from a first position to a second position and vice versa. In the second position, a person supported by the seating support is exposed to a source of radiation to a lesser extent than in the first position.

The first position may provide a seating position, i.e. a position wherein the user is provided with more space to get seated on the seat support surface. In the first position, the X-ray shield may for example be moved to the side such that shielding is reduced or not provided at all. On the other hand, in this shield position, a user has relatively easy access to the seating surface and/or a seated user may have unimpeded access to a patient on the table.

The second position provides a usage or shielding position, i.e. a position where the user is effectively shielded from radiation. In the second position, the X-ray shield is positioned to be shielding effective such that an amount of scatter radiation received by the user is reduced as much as possible.

In an example, in the first position, a distance between the X-ray shield and the seating support is larger than in the second position.

According to a further example, the at least one X-ray shield is rotatable around the seating support arrangement. In an option, the at least one X-ray shield is rotatable over at least 180°, preferably over 360°.

The rotation allows an optimal and intuitive positioning of the shielding, and also storing away, e.g. behind the user, while ensuring that the shielding is always in reach of access for the user. The 360° rotatable shield offers freedom of movement and the ability to freely rotate the shield between the seating position, a shielding position and an optional storage position.

The rotation of the X-ray shield may be provided along a horizontally arranged circular movement path. For example, when a user is seated on the seating support, the X-ray shield rotates around a rotation axis substantially coinciding with a length axis of the seated user's upper body.

In an example, for the rotation, the X-ray shielding arrangement comprises a cantilevering arm that is rotatably mounted to the base support structure below the seating support. The cantilevering arm is provided with an upwardly extending support to which a further, side-wards cantilevering arm is connected to carry an X-ray shield in a hanging manner.

According to an example, the at least one X-ray shield is arc-shaped. In addition, or alternatively, the at least one X-ray shield is made of soft material that is hanging from an upper support.

According to an example, the at least one X-ray shield is pivotable around a vertical pivoting axis.

In an example, the seat support surface and the at least one X-ray shield each are provided with a height adjustment to be height adjustable. As an option, it is provided that the height adjustment of the at least one X-ray shield is coupled to the height adjustment of the seat support surface such that the at least one X-ray shield is height-coupleable to the seat support surface.

In an example, the pivoting movement of the X-ray shield is provided in addition to the rotational movement of the X-ray shield. In another example, the pivoting movement of the X-ray shield is provided instead of the rotational movement of the X-ray shield.

According to an example, a sternum support arrangement is provided that comprises a sternum support surface which is configured for supporting a sternum of a user. In an option, the sternum support surface is rotatable around the seating support arrangement. In a further option, the sternum support surface is rotatable over at least 180°, preferably over 360°.

According to an example, an arm support arrangement is provided that comprises at least one lower arm support surface which is configured for supporting a lower arm of a user. In an option, the lower arm support surface is rotatable around the seating support arrangement. In a further option, the lower arm support surface is rotatable over at least 180°, preferably over 360°.

In an example, both functional parts (protection and support) are approached from the left side and so they will not interfere between the legs. This provides further freedom of movement and the ability to rotate the device around the body of the user.

The integration of support and X-ray protection creates an improved combination of functionalities for cathlab staff.

The shape of the sternum support is based on the shape of the sternum such that it will only put pressure on the sternum and not on the soft tissue and muscles around it. Hence, a numb feeling over time is prevented or at least reduced.

According to an example, the base support structure is provided as a mobile chair base that comprises at least three swivel pulleys.

According to the present invention, also a medical laboratory equipment arrangement is provided. The arrangement comprises an X-ray imaging system and an ergonomic support device according to one of the preceding examples. The X-ray imaging system comprises an X-ray detector and an X-ray source for radiating of a patient arranged on a patient support. The ergonomic support device is configured to support a user in vicinity to the patient during X-ray radiating activities for imaging generating purposes.

According to the present invention, also a method for X-ray imaging of a patient is provided. The method comprises the following steps:
a) arranging a patient at least partly on a patient support;
b) radiating the patient with X-ray radiation and detecting the resulting radiation for generating X-ray image data; and
c) supporting a user with an ergonomic support device according to one of the previous examples at least during the radiating step b).

According to an aspect, a stool support is provided that allows a standing position while still being supported. A movable X-ray shield provides additional X-ray protection meaning a relief for the user's personal X-ray protection like a front apron, comprising X-ray absorbing materials like lead. The movability allows increased flexibility for the user and provides adaptable and thus optimized X-ray shielding where necessary.

The ergonomic support device provides support, e.g. for cathlab physicians, such that for performing their jobs, which might include standing for long periods of time, and support means relief, since a lighter lead apron can be used while standing and being arranged behind the X-ray shield such that sufficient (and required) protection is offered. Thus, an increased support option is provided that results in an increased range of postures while still providing protection. For example, a leaning forward posture of a physician is still supported as an example, which reduces major muscle tension in the lower back.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
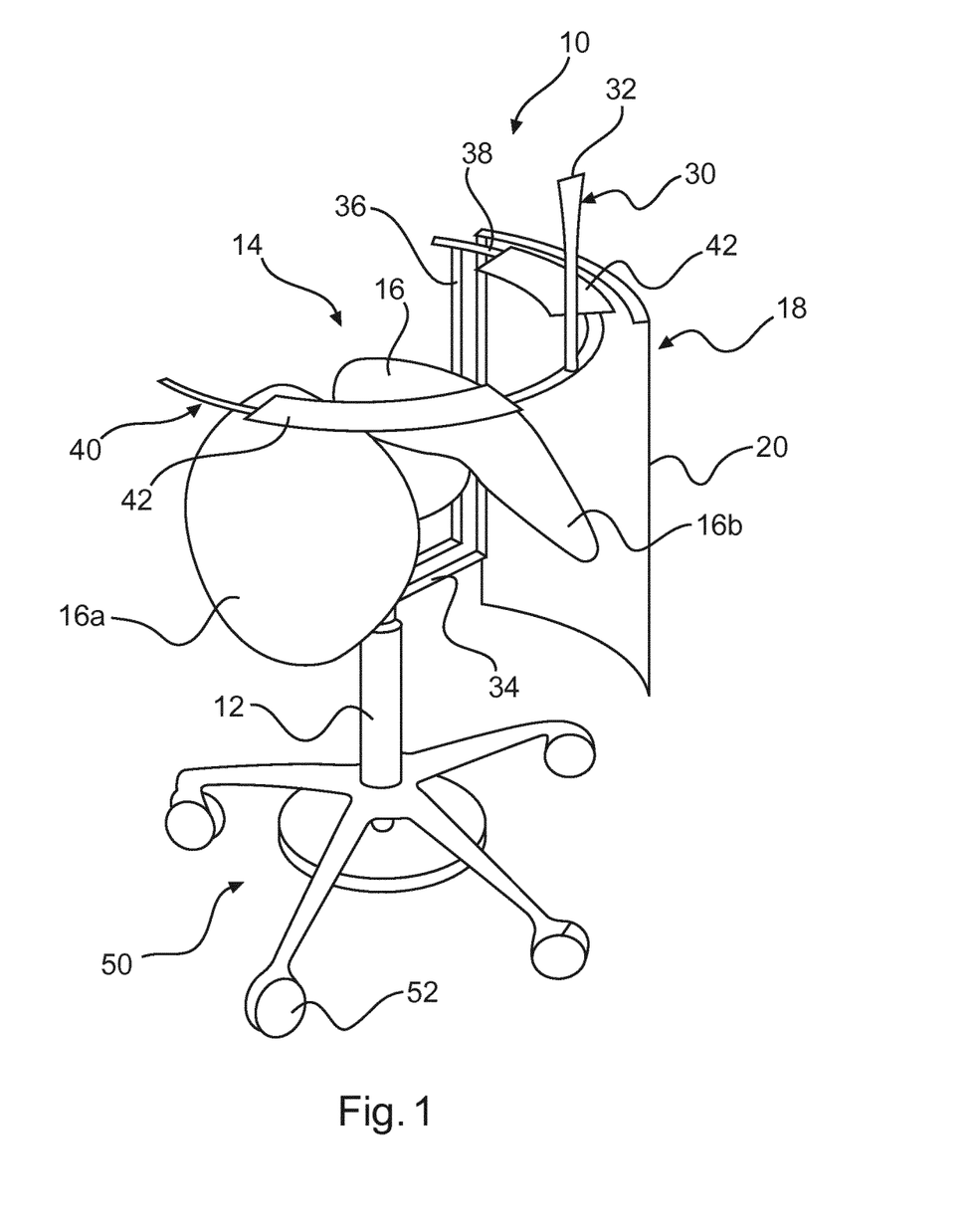
FIG. 1 shows a perspective view of an example of an ergonomic support device with several options.

FIG. 1 shows an ergonomic support device 10 for users in medical environment. The support device 10 comprises a base support structure 12. The support device 10 also comprises a seating support arrangement 14 that comprises a seat support surface 16 that is configured for supporting a buttocks area of a user. The seat support surface may be provided as a single piece saddle or (as shown), as e.g. a two-piece saddle type seat. The support device 10 also comprises an X-ray shielding arrangement 18 that comprises at least one X-ray shield 20 that is configured for shielding at least a part of an X-ray radiation to which a user is exposed to while supported by the support surface. The support structure 12 provides mechanical support for the seating support arrangement and the X-ray shielding arrangement. The at least one X-ray shield 20 is movably mounted to the base support structure to be adjustable in its position relative to a user at least partly resting on the seat support surface.

The at least one X-ray shield 20 is movable from a first position P1 (see FIG. 3) to a second position P2 and vice versa. In the first position, a user has easy access to the support surface 16 in order to seat himself thereon, without being obstructed or impeded by the shield 20. In the second position, a person seated on the support surface 16 is effectively shielded from a source of X-ray radiation. Thus, in this shield position, incident radiation, in particular scattered X-ray radiation emanating from a patient being treated, is eliminated or at least reduced.

In an example, the seat support surface 16 is provided as a saddle as shown. For example, the saddle comprises a two-part saddle formation with a first saddle portion 16a and a second saddle portion 16b. However, other types of surfaces to sit respectively to rest on are also provided in further examples.

Figure 2:
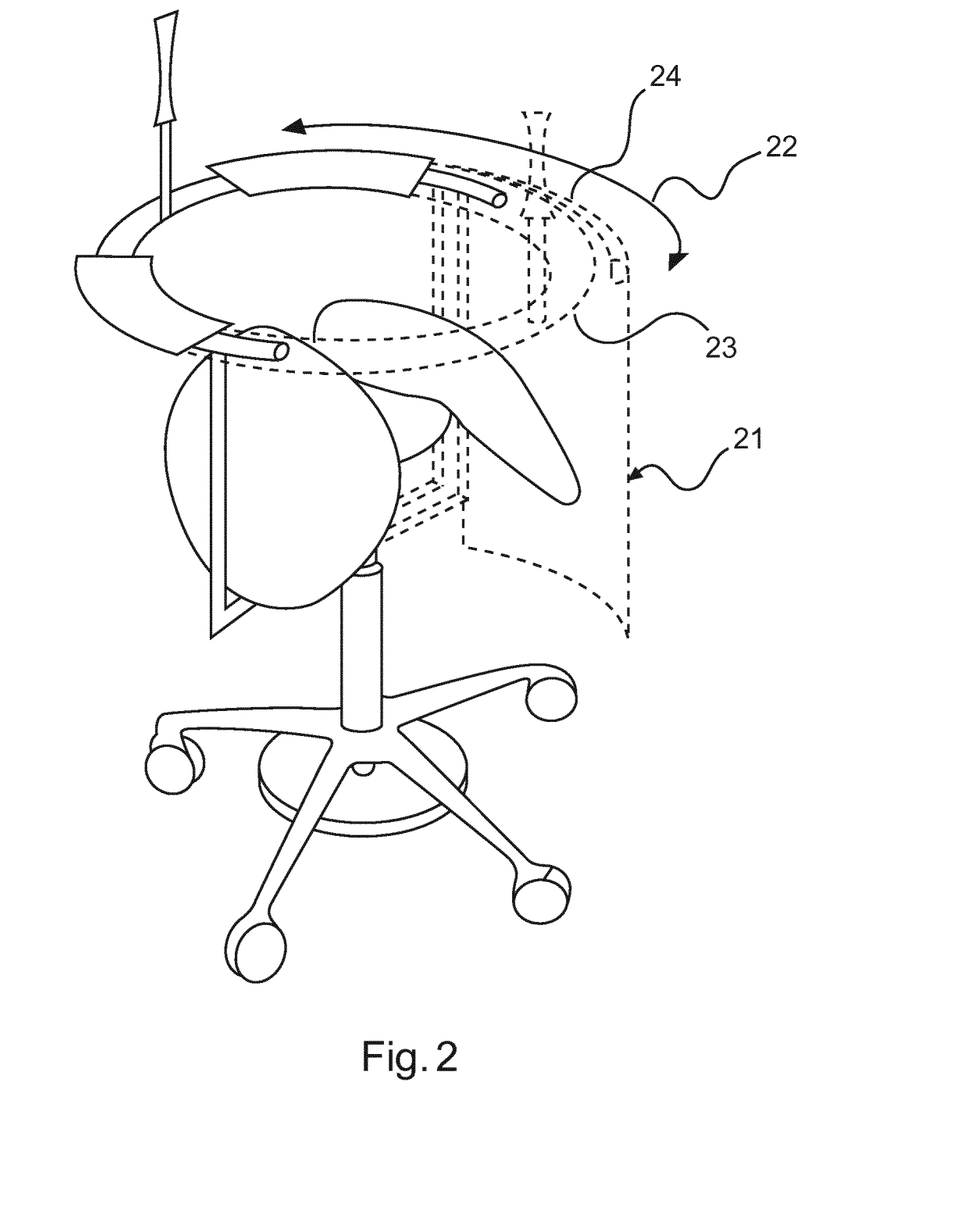
FIG. 2 shows an example of an ergonomic support with movable components.

As shown in FIG. 2, in an option, the at least one X-ray shield 20 is rotatable around the seating support arrangement, as indicated with rotating arrow 22. Preferably, the at least one X-ray shield 20 is rotatable over at least 180°, preferably over 360°.

As an option, the at least one X-ray shield 20 is arc-shaped.

In an example, the X-ray shield is concentrically arc-shaped around the point of rotation. This provides minimal use of space in the cathlab environment.

In an example, the X-ray shield is provided curtain-like such that the soft, cloth-like shield is capable of adapting its form to the user's legs, in particular the user's knees if they are abutting the X-ray shield.

In an example, the X-ray shielding arrangement comprises a set of differently sized X-ray shields that can be exchanged allowing to provide scaled X-ray shielding depending of the user's size and shape. For example, shield segments may be provided with a different width and/or a different length.

As a further option, the at least one X-ray shield 20 is made of soft material that is hanging from an upper support 24.

In FIG. 2, the X-ray shield is shown in hashed lines. The movability is indicated by showing the arm support arrangement with its surfaces turned around to the back side of the chair (when considering the saddle orientation as an indication of the user's main orientation during e.g. treatment of a patient. In an option, the X-ray shield shown in hashed lines can also be moved.

Figure 3:
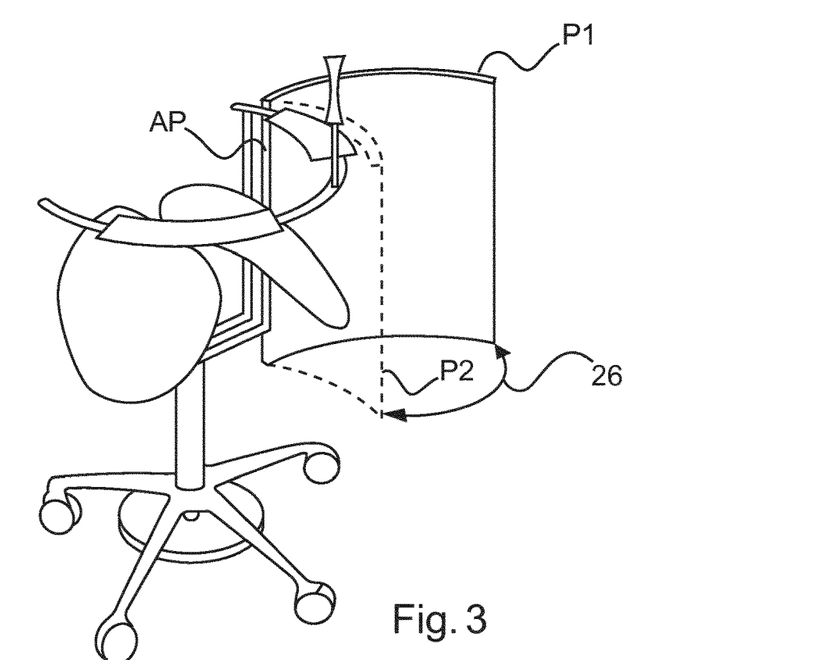
FIG. 3 shows an example of an ergonomic support with a movable X-ray shield.

As shown in FIG. 3, in an option, the X-ray shield 20 is pivotable (indicated with pivoting arrow 26) around a vertical pivoting axis $A_P$. The X-ray shield 20 can thus be moved to the side for easy access to the seat surface.

The first position P1 is indicated in FIG. 3 with hashed lines and the second position P2 is shown in through-lines.

Figure 4:
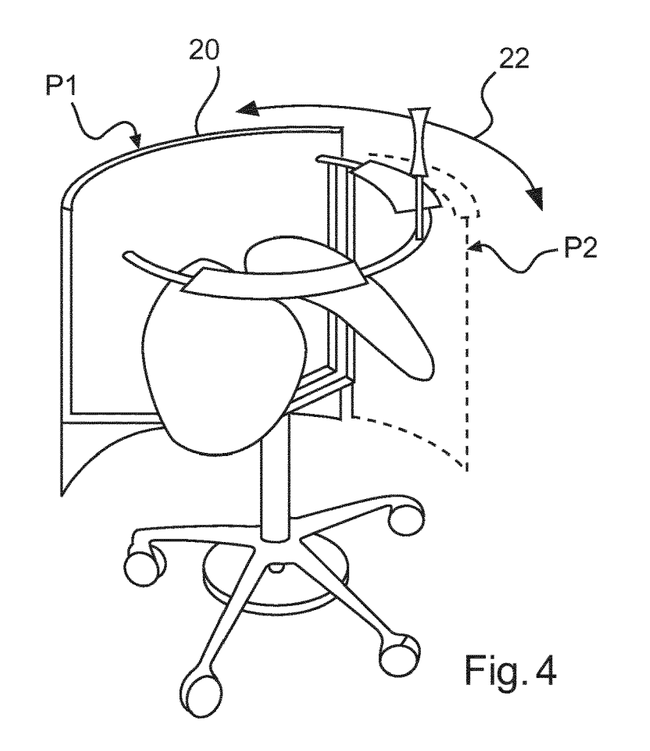
FIG. 4 shows an example of an ergonomic support with a movable X-ray shield.

FIG. 4 shows an arrangement of the X-ray shield 20 so-to-speak behind the user and thus moved aside for easy access to the seat surface. The X-ray shield is thus shown in the first position P1. The second position P2 is indicated in FIG. 3 with hashed lines.

Of course, in FIGS. 3 and 4, as an option the arm support arrangement may also be rotated and thus moved.

As another option, a sternum support arrangement 30 is provided that comprises a sternum support surface 32 which is configured for supporting a sternum of a user. For example, the sternum support surface 32 is rotatable around the seating support arrangement. Preferably, the sternum support surface 32 is rotatable over at least 180°, preferably over 360°.

In an option, the seat support surface 16 and the sternum support surface 32 each are provided with a height adjustment to be height adjustable. As an option, it is provided that the height adjustment of the sternum support surface is coupled to the height adjustment of the seat support surface such that the sternum support surface is height-coupleable to the seat support surface.

The rotation of the sternum support surface is provided along a horizontally arranged circular movement path.

In an example, for the rotation, the sternum support arrangement comprises a cantilevering arm 34 that is rotatably mounted to the base support structure below the seating support. The cantilevering arm is provided with an upwardly extending support 36 to which a further, side-wards cantilevering 38 arm is connected. The sternum support surface is carried by this side-wards cantilevering arm. The sternum support surface is projecting slightly inclined upwardly.

In an example, an arm support arrangement 40 is provided that comprises at least one lower arm support surface 42 which is configured for supporting a lower arm of a user. In an option, the lower arm support surface 42 is rotatable around the seating support arrangement. Preferably, the lower arm support surface is rotatable over at least 180°, preferably over 360°.

The lower arm support surface is, in particular, provided as support for the user's elbows. The small shape of the sternum support will give the user the ability to move its arms freely.

In a further option, the arm support surfaces and the X-ray shield are mounted to a common cantilevering arm structure and are moved together.

In a still further option, the arm support surfaces are provided to be attached to a common cantilevering arm structure. The X-ray shield is movably mounted, e.g. in a sliding and/or pivoting manner, to an upper rail like part of the common cantilevering arm structure. Hence, independent adjustments of arm support surfaces and X-ray shielding are possible.

In an example, the seat support surface and the lower arm support surface each are provided with a height adjustment to be height adjustable. As an option, it is provided that the height adjustment of the lower arm support surface is coupled to the height adjustment of the seat support surface such that the lower arm support surface is height-coupleable to the seat support surface.

The rotation of the lower arm support surface is provided along a horizontally arranged circular movement path.

In an example (not shown in detail), for the rotation, the arm support arrangement comprises a cantilevering arm that is rotatably mounted to the base support structure below the seating support. The cantilevering arm is provided with an upwardly extending support to which a further, side-wards cantilevering arm is connected. The arm support surface is provided by this side-wards cantilevering arm.

In another example, the arm support arrangement is formed by the side-wards cantilevering arm that carries the sternum support surface, as shown in FIG. 1.

In an example, the seat support surface and at least one of the group of: the at least one X-ray shield, the sternum support surface and the lower arm support surface each are rotatably mounted. In an option, the seat support surface and at least one of the group of: the at least one X-ray shield, the sternum support surface and the lower arm support surface are rotatable independently from each other. In an option, at least two of the group of: the seat support surface, the at least one X-ray shield, the sternum support surface and the lower arm support surface are rotatable around a common central rotation axis.

In another example, the seat support surface and at least one of the group of: the at least one X-ray shield, the sternum support surface and the lower arm support surface rotate together. As an option, it is provided that the rotational movements are directly coupled.

In an example, the seat support surface, the at least one X-ray shield, the sternum support surface and the lower arm support surface are concentrically mounted to the base support structure.

Figures 5, 6:
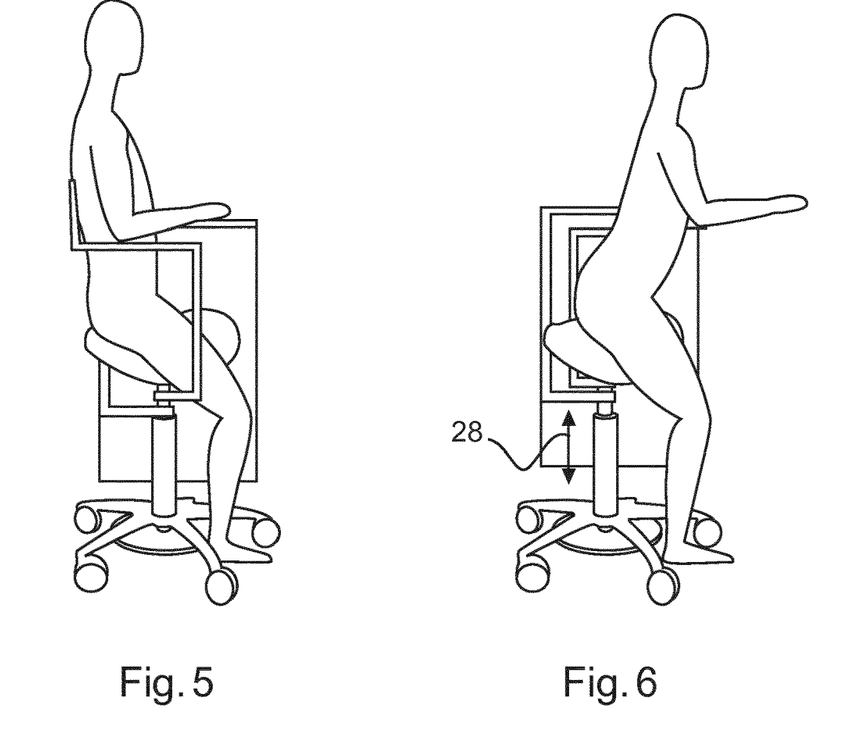
FIGS. 5 and 6 show examples of postures of a user on an example of the ergonomic support.

In an example, the seat support surface and at least one of the group of: the at least one X-ray shield, the sternum support surface and the lower arm support surface each are provided with a height adjustment to be height adjustable (see arrow 28 in FIG. 6). In an option, the height adjustment of the seat support surface is coupled to the height adjustment of at least one of the group of: the at least one X-ray shield, the sternum support surface and the lower arm support surface such that the seat support surface is height-coupleable with at least one of the group of: the at least one X-ray shield, the sternum support surface and the lower arm support surface.

Thus, by providing a sternum support for a user which can be attached to a stool, the physician can lean forward without generating too much muscle tension in the lower back. Extra protection is available as an integrated solution which makes it easy to position and which moves along with the user.

In an option, the base support structure is provided as a mobile chair base 50 that comprises at least three swivel pulleys 52. In an example, the mobile chair base comprises at least five pulleys. The pulleys may be provided as brake-when-loaded casters.

In an example, the base support structure is provided as a mobile structure.

In another example, the base support structure is fixedly mountable to a floor structure.

In an example, the base support structure is height adjustable to provide a seating support for the user in a range between a first position of the seat support surface and a second position of the seat support surface. The first position is a lower position and the second position is an upper position. The lower position allows a sitting position of the user and the upper position allows a standing position of the user.

In an example, the lower position allows a sitting position for a 5%-Japanese-female user, and also for a 95%-US-male user. In another example, the upper position allows a standing position or a nearly full-standing position for a 5%-Japanese-female user, and also for a 95%-US-male user.

FIG. 5 shows a user 60 (see FIG. 7) in a more sitting position, whereas FIG. 6 shows the user 60 in a more standing position, but in both positions supported by the support seat surface.

In FIG. 5, the sternum support surface is shown moved to the rear side, in FIG. 5 to the left side, and thus behind the user. The user can thus lean backwards against the sternum support surface.

Figure 7:
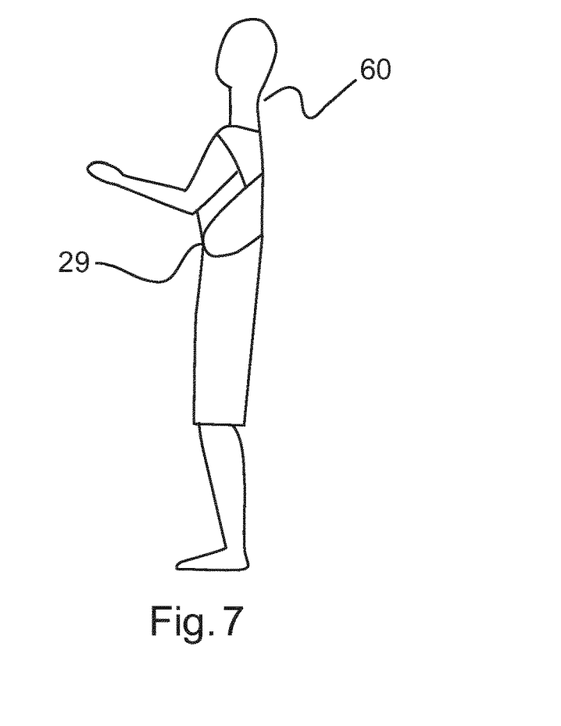
FIG. 7 shows a user wearing a front apron.

In FIG. 6, the sternum support surface is shown moved to the front side, in FIG. 6 to the right side, and thus in front of the user. The user can thus lean forwards against the sternum support surface In both positions, the user can where a front apron 29, which is indicated in FIG. 7 for a user when approaching an ergonomic support device for users in medical environment.

Figure 8:
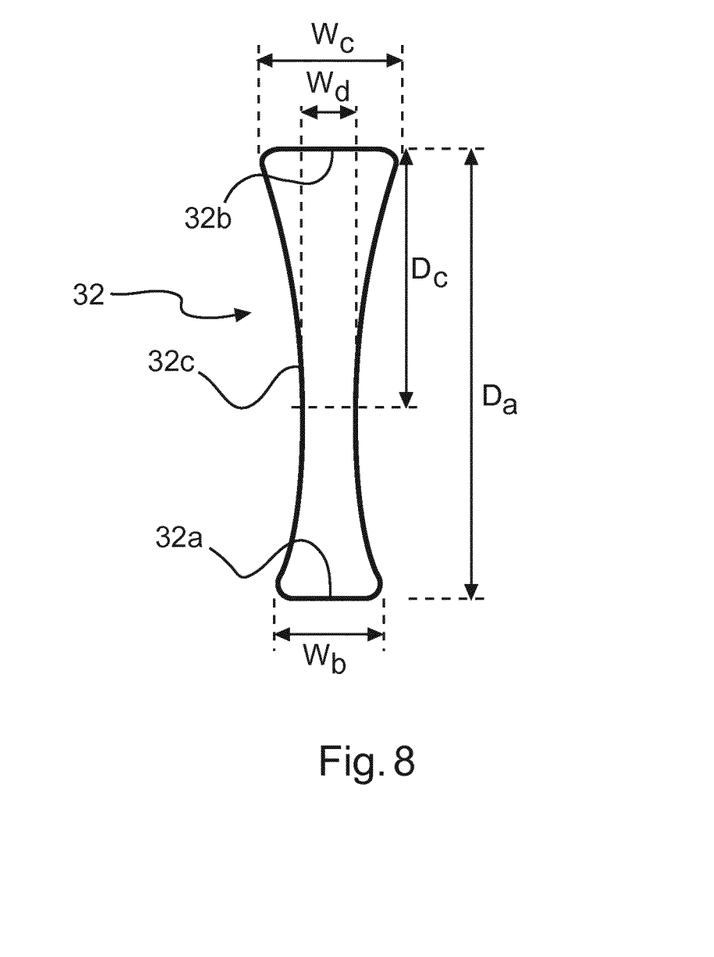
FIG. 8 shows an example of a sternum support surface in a schematic front view.

As shown in FIG. 8, in an example, the sternum support surface 32 has a vertically oriented longitudinal shape for providing a contact surface essentially exclusive for the sternum of the user.

In an example, the sternum support surface 32 has a vertically oriented longitudinal shape for providing a contact surface essentially exclusive for the sternum of the user. In another example, the sternum support surface has a shape of approximately 3 cm width and approximately 10 cm height.

The sternum support surface can be provided to be replaceable. For example, different sizes, and/or forms with different width/height ratio are provided.

In an example the sternum support surface is provided with a lower end 32a and an upper end 32b and with a central portion 32c between lower and upper end. In an example, a width $W_b$ of the lower end is less than a width $W_c$ of the upper end. In a further example, a width $W_d$ of the central portion is less than the width of the lower end, and also less than the width of the upper end. In an example, the side portions between upper and lower end are shaped in a concaved manner.

In an example, the central portion is arranged slightly lower than half the distance between the upper end and the lower end, i.e. an upper distance $D_e$ form the central portion to the upper end is larger than half of the overall distance Da form the upper end to the lower end.

In an example, the sternum support surface is provided to be flexible to conform with the user's sternum contour. In an example, the sternum support surface is mounted to be pivotable around a central horizontal axis to allow differently inclined orientations of the sternum support surface.

It must be noted that besides these features, the figures show further options that may be provided. It is in particular noted that the rotatable X-ray shield may be provided without the sternum support.

Figure 9:
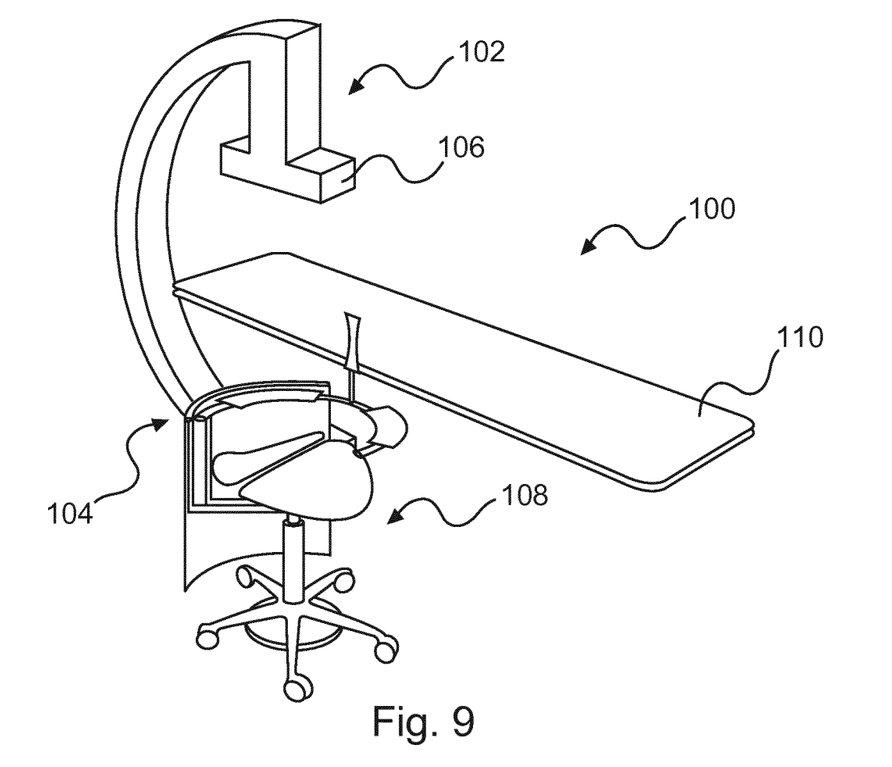
FIG. 9 shows an example of a medical laboratory equipment arrangement with an ergonomic support device.

FIG. 9 schematically shows an example of a medical laboratory equipment arrangement 100. The arrangement comprises an X-ray imaging system 102 and an ergonomic support device 108 that is provided as an example of the ergonomic support device 10 described above. The X-ray imaging system 102 comprises an X-ray detector 106 and an X-ray source 104 (hidden behind the ergonomic support device) for radiating of a patient arranged on a patient support 110, e.g. a patient table. The ergonomic support device is configured to support a user in vicinity to the patient during X-ray radiating activities for imaging generating purposes.

The ergonomic support device 104 is shown with the sternum support moved to the front in view of the patient table, and the X-ray shielding is moved to the side.

Figure 10:
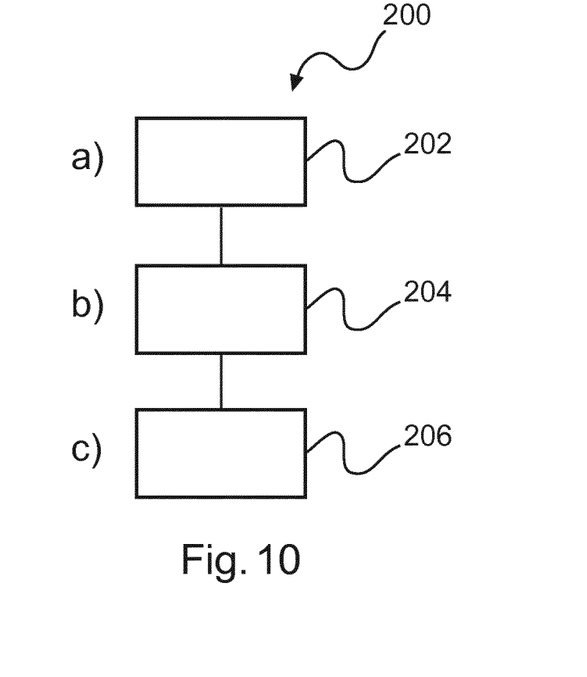
FIG. 10 shows an example of a method for X-ray imaging of a patient.

FIG. 10 shows an example of a method 200 for X-ray imaging of a patient. The method comprises the following steps: In a first step 202, also referred to as step a), a patient is arranged at least partly on a patient support. In a second step 206, also referred to as step b), the patient is radiated with X-ray radiation and detecting the resulting radiation for generating X-ray image data. In a third step 206, also referred to as step c), a user is supported with an ergonomic support device according to one of the above-described examples during the radiating step b).

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An ergonomic support device for users in a medical environment, the support device comprising:
   a seating support arrangement comprising a seat support surface configured to support a buttocks area of a user of X-ray equipment;
   an X-ray shielding arrangement comprising at least one X-ray shield configured to shield at least a part of an X-ray radiation to which the user is exposed while supported by the seat support surface; and
   a base support structure configured to provide mechanical support for the seating support arrangement and the X-ray shielding arrangement,
   wherein the at least one X-ray shield is movably mounted to the base support structure to be adjustable in position relative to the user at least partly resting on the seat support surface, and the at least one X-ray shield is i) rotatable around the seating support arrangement and/or ii) pivotable around a vertical pivoting axis at which the at least one X-ray shield is movably mounted to the base support structure, wherein the at least one X-ray shield is movable from a first seating position in which the user has access to the seat support surface to a second shielding position in which the user supported by the seat support surface is shielded from X-ray radiation, and vice versa.

2. The ergonomic support device according to claim 1, wherein the at least one X-ray shield is rotatable around the seating support arrangement.

3. The ergonomic support device according to claim 2, wherein the at least one X-ray shield is rotatable over at least 180°.

4. The ergonomic support device according to claim 1, wherein the at least one X-ray shield is arc-shaped; and/or wherein the at least one X-ray shield is made of soft material that is hanging from an upper support.

5. The ergonomic support device according to claim 1, wherein the at least one X-ray shield is pivotable around the vertical pivoting axis.

6. The ergonomic support device according to claim 1, further comprising a sternum support arrangement that comprises a sternum support surface configured to support a sternum of the user, wherein the sternum support surface is rotatable around the seating support arrangement, and
wherein, the sternum support surface is rotatable over at least 180°.

7. The ergonomic support device according to claim 6, wherein the sternum support surface has a vertically oriented longitudinal shape for providing a contact surface exclusive for the sternum of the user.

8. The ergonomic support device according to claim 1, further comprising an arm support arrangement that comprises at least one lower arm support surface configured to support a lower arm of the user;
wherein the lower arm support surface is rotatable around the seating support arrangement, and
wherein the lower arm support surface is rotatable over at least 180°.

9. The ergonomic support device according to claim 1,
wherein the seat support surface and at least one of the group of: the at least one X-ray shield, a sternum support surface, and a lower arm support surface each are rotatably mounted,
wherein the seat support surface and at least one of the group of: the at least one X-ray shield, the sternum support surface, and the lower arm support surface are rotatable independently from each other, and
wherein at least two of the group of: the seat support surface, the at least one X-ray shield, the sternum support surface, and the lower arm support surface are rotatable around a common central rotation axis.

10. The ergonomic support device according to claim 1,
wherein the seat support surface and at least one of the group of: the at least one X-ray shield, a sternum support surface, and a lower arm support surface each are provided with a height adjustment to be height adjustable, and
wherein the height adjustment of the seat support surface is coupled to the height adjustment of at least one of the group of: the at least one X-ray shield, the sternum support surface, and the lower arm support surface, such that the seat support surface is height-coupleable with at least one of the group of: the at least one X-ray shield, the sternum support surface, and the lower arm support surface.

11. The ergonomic support device according to claim 1, wherein the base support structure is provided as a mobile chair base that comprises at least three swivel pulleys.

12. The ergonomic support device according to claim 1,
wherein the base support structure is height adjustable to provide seating support for the user in a range between a first position of the seat support surface and a second position of the seat support surface, the first position being a lower position and the second position being an upper position, and
wherein the lower position allows a sitting position of the user and the upper position allows a standing position of the user.

13. A medical laboratory equipment system, comprising:
an X-ray imaging system; and
the ergonomic support device according to claim 1,
wherein the X-ray imaging system comprises an X-ray detector and an X-ray source for radiating a patient arranged on a patient support, and
wherein the ergonomic support device is configured to support the user in vicinity to the patient during X-ray radiating activities for imaging generating purposes.

* * * * *